United States Patent [19]

Nicolaou et al.

[11] 4,291,166
[45] Sep. 22, 1981

[54] PHARMACEUTICALLY ACTIVE 6,9-THIAPROSTACYCLIN ANALOGS AND DERIVATIVES THEREOF

[75] Inventors: Kyriacos C. Nicolaou, Philadelphia; William E. Barnette, Levittown, both of Pa.; Ronald L. Magolda, Vineland, N.J.

[73] Assignee: Research Corporation, New York, N.Y.

[21] Appl. No.: 886,141

[22] Filed: Mar. 13, 1978

[51] Int. Cl.$^3$ ............................................. C07D 333/78
[52] U.S. Cl. ..................................... 549/51; 424/275; 549/53
[58] Field of Search ...................... 260/332.1, 332.2 A; 549/51, 53

[56] References Cited

U.S. PATENT DOCUMENTS 3,881,017  4/1975  Vlattas ............................ 260/332.1
4,125,713  11/1978  Nelson ........................... 260/346.22

OTHER PUBLICATIONS

Johnson, Roy A. et al., "The Chemical Structure of Prostaglandin X (Prostacyclin)". Prostaglandins, (1976) Vol. 12, No. 6, pp. 915-928.
Shibasaki, Masakatsu et al., "Synthesis of 9(0)-thiaprostacyclin", Tetrahedron Letters, No. 6, 559-562, 1978.
Shibasaki, Masakatsu et al., "Intramolecular Sulfenyl Addition Promising a New Synthetic Route to 9(0)--thiaprostacyclin", Tetrahedron Letters, No. 46, pp. 4037-4040, (1977).

Nicolaou, Kyriacus C. et al., Angew. Chemie, Int. Ed. (Eng.), vol. 17, (1978), pp. 293-378.
Nicolaou, Kyriacus C. et al., J. Am. Chem. Soc., vol. 99, pp. 7736-7738, (Nov. 9, 1977).
*Chemical and Engineering News*, Sep. 5, 1977, pp. 6, 19 & 22.

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

Stable biologically active 6,9 α-thiaprostacyclin derivatives having the formula

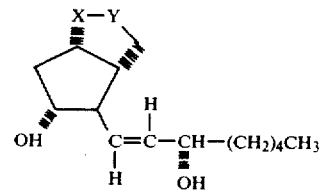

wherein
X represents $>S$, $>SO$ or $>SO_2$;
Y represents (E) and
(Z)—$>C=CH-CH_2CH_2CH_2COOR$,
(E)—$>CH-CH=CH-CH_2CH_2COOR$ or
$>CH-CH_2-CH_2-CH_2-CH_2COOR$; and
R represents hydrogen, a pharmaceutically acceptable cation or a pharmaceutically acceptable lower alkyl group.

15 Claims, No Drawings

PHARMACEUTICALLY ACTIVE 6,9-THIAPROSTACYCLIN ANALOGS AND DERIVATIVES THEREOF

BACKGROUND OF THE INVENTION

1. Field of the Invention

This invention relates to stable 6,9α-thiaprostacyclin derivatives which are active as inhibitors of blood platelet aggregation and/or which show arterial constriction activities.

2. Description of the Prior Art

The prostaglandins were first discovered in the 1920's and have proven since then to be among the most ubiquitous pharmaceutically active compounds ever tested. Their use and the use of analogs and derivatives thereof, has been suggested in as wide a range of applications as fertility control, induction of labor, regulation of blood pressure, regulation of blood clotting, control of asthma, anticonvulsion, antidepressants, and many others. A new compound has recently been discovered (Nature 263, 663 (1976); *Prostaglandins*, vol. 12, 685 and 715 (1976); Chem. and Engineering News, Dec. 20, 1976) which belongs to the general family of prostaglandins. The compound has been named prostacyclin and its structure has been proven by synthesis (Johnson, et al, *Prostaglandins*, 12, 915 (1976); Corey, et al, J. Amer. Chem. Soc., 99, 2006 (1977)) to be that of formula I. (The numbering system for prostacyclins is given for reference):

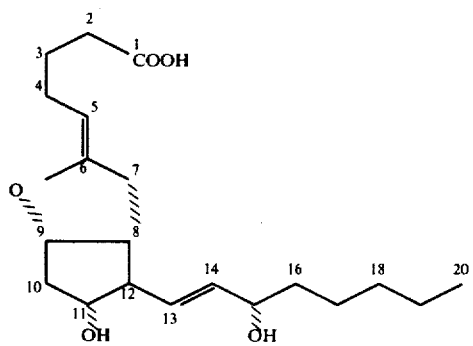

Its generic name is 6,9α-oxido-11α,15α-dihydroxyprosta(Z)5,E(13)dienoic acid. Prostacyclin is the most potent inhibitor of blood platelet aggregation of all the prostaglandins discovered to date. It has also been shown that prostacyclin destroys platelet aggregates after they have formed and that it has, in addition, a powerful action as a dilator of blood vessels. Prostacyclin thus appears to act in exactly opposite ways to thromboxane $A_2$ another recently discovered member of the prostaglandin family. Thromboxane $A_2$ causes platelet aggregation and simultaneously act as powerful constrictor of arteries. Both prostacyclin and thromboxane $A_2$ are derived biosynthetically from a common intermediate, called endoperoxide and they are decomposed by water to prostaglandins. The balance between the levels of prostacyclin and thromboxane $A_2$, appears to maintain a finely tuned equilibrium between blood platelet aggregation versus dissolution and arterial constriction versus dilation.

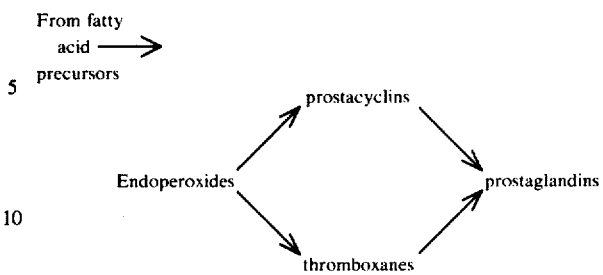

The use of prostacyclins has been suggested in the treatment of blood clotting in diseased vessels of patients with cardiovascular problems. Since prostacyclin has retroactive action and not only inhibits blood clotting but also dissolves already formed clots, it can be used in heart attack cases and artherosclerosis. Increased susceptibility of platelets to aggregation accompanies vascular complications in diabetes, in cerebral strokes associated with essential hypertension and in post heart attack cases. These are other areas where prostacyclin activity can be highly beneficial. The main drawback of the use of prostacyclin for these applications is its very short biological half-life of 2 minutes. This prevents the externally provided drug from reaching its target tissues intact. The need to maintain the drug in a totally anhydrous condition also prevents its ready shipment, storage and testing for pharmacological applications. If an analog or derivative of prostacyclin can be formed which is stable and shows similar effects on blood platelets and arteries, it would have wide applications in pharmacology and the treatment of cardiovascular and related diseases. Another application for a stable analog of prostacyclin would be its use as an inhibitor of blood platelet aggregation in externally circulated blood by kidney dialysis machines or heart-lung machines.

SUMMARY OF THE INVENTION

Accordingly, it is an object of the invention to provide pharmacologically active compounds useful in the treatment of blood clotting and other related cardiovascular diseases. A further object of the invention is to provide pharmacologically active compounds which are stable analogs and/or derivatives of prostacyclin.

Another object of the invention is to provide stable biologically active prostacyclin analogs which contain a sulfur atom, a sulfoxide group or a sulfone group in replacement of the 6,9α-oxido group of natural prostacyclin. Still another object of the invention is to provide stable biologically active prostacyclin analogs which contain, in addition to a sulfur, sulfoxide or sulfone group at the 6,9α position, a double bond at the $C_4$ position. Yet a further object of the invention is to provide stable biologically active prostacyclin analogs which contain, in addition to a sulfur, sulfoxide or sulfone group at the 6,9α position, a single bond at position $C_5$. These and other objects of the invention, which will become obvious hereinafter have been attained by preparing stable 6,9αthiaprostacyclin derivatives having the formula

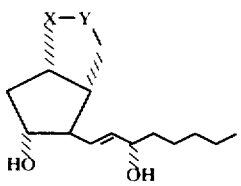

wherein

X represents >S, >SO or >SO$_2$;

Y represents (E) and
(Z)->C=CH—CH$_2$—CH$_2$—CH$_2$COOR,
(E)->CH—CH=CH—CH$_2$CH$_2$COOR or
>CH—CH$_2$—CH$_2$—CH$_2$—CH$_2$COOR and R represents hydrogen, pharmaceutically acceptable cation or a pharmaceutically acceptable lower alkyl group. The compounds of the present invention are stable to attack by water, they show activity in the inhibition of blood platelets, are antagonists for natural prostacyclin and, as opposed to natural prostacyclin and in analogy to thromboxane A$_2$, they show vasoconstrictor activity.

DESCRIPTION OF THE PREFERRED EMBODIMENTS

The compounds of the present invention include prostacyclin derivatives of the formula

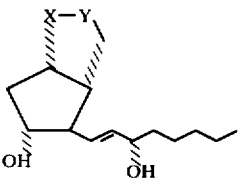

wherein

X = >S, >SO, >SO$_2$; and

Y = (E) and
(Z)->C=CH—CH$_2$CH$_2$CH$_2$COOR;
(E)->CH—CH=CH—CH$_2$CH$_2$COOR;
>CH—CH$_2$CH$_2$CH$_2$CH$_2$COOR; and R = hydrogen or pharmaceutically acceptable cation or a pharmaceutically acceptable lower alkyl group.

Pharmaceutically acceptable cations useful for the purposes of this invention are those with pharmaceutically acceptable metal cations, ammonium, amine cations or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and loweralkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl) aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

Pharmaceutically acceptable lower alkyl groups are those derived from C$_1$-C$_{10}$ hydrocarbyl residues, especially C$_1$-C$_4$. Most preferred are methyl and ethyl groups.

It should be noted that where X=>SO, the rigid configuration of the sulfur-oxygen bond, generates two distinct diastereomers. These isomers can be separated and have distinct chemical and biological properties. Similarly, when Y=>C=CH—CH$_2$CH$_2$CH$_2$COOR, the double bond can have two distinct geometric configurations, 5(Z) and 5(E). These two configurations generate two compounds with distinct chemical and biological properties.

When Y=>CH—CH=CH—CH$_2$CH$_2$COOR, the asymmetric center at C-6 can exist in 2 epimeric forms which also causes the product to exist in 2 distinct diastereomeric forms. These forms have different physical, chemical and biological properties.

When Y=>CH—CH$_2$CH$_2$CH$_2$CH$_2$COOR, the asymmetric center at C-6 can also exist in 2 epimeric forms. This also generates 2 diastereomeric, distinct compounds with different properties.

When X=>S and Y=5(Z)->C=CH—CH$_2$CH$_2$CH$_2$COOR, the resulting product is 5(Z)-6,9-thiaprostacyclin, the exact 6,9-thia analog of natural prostacyclin. This compound, in the form of its sodium salt aqueous solutions is stable for long periods of time and can be easily bioassayed. It shows platelet inhibitory activity in vitro and constricts isolated cat coronary artery.

Other representative compounds within the scope of this invention are:

5(E)-6,9α-thiaprostacyclin methyl ester and sodium salt

5(Z)-6,9α-sulfoxa-prostacyclin methyl ester and sodium salt (2 diastereomers)

5(E)-6,9α-sulfoxa-prostacyclin methyl ester and sodium salt (2 diastereomers)

5(Z)-6,9α-sulfo-prostacyclin methyl ester and sodium salt (2 diastereomers)

5(E)-6,9α-sulfo-prostacyclin methyl ester and sodium salt

4(E)-6,9α-sulfo-thiaisoprostacyclin methyl ester and sodium salt 5,6-dihydro-6,9α-thiaprostacyclin methyl ester and sodium salt (2 diastereomers)

5,6-dihydro-6,9α-sulfoxa-prostacyclin methyl ester and sodium salt (4 diastereomers)

5,6-dihydro-6,9α-sulfo-prostacyclin methyl ester and sodium salt (2 diastereomers)

4(E)-6,9α-thiaisoprostacyclin methyl ester and sodium salt (2 diastereomers)

4(E)-6,9α-sulfoxathiaisoprostacyclin methyl ester and sodium salt (4 diastereomers)

The compounds of the present invention can be prepared by cyclization of appropriately protected 5(Z) and 5(E), 9α-thioprostaglandin derivatives II-Z and II-E in the presence of acids, halogens or phenyl selenenyl halides. The reaction yields 6,9α-thiaprostacyclin derivatives of formula III.

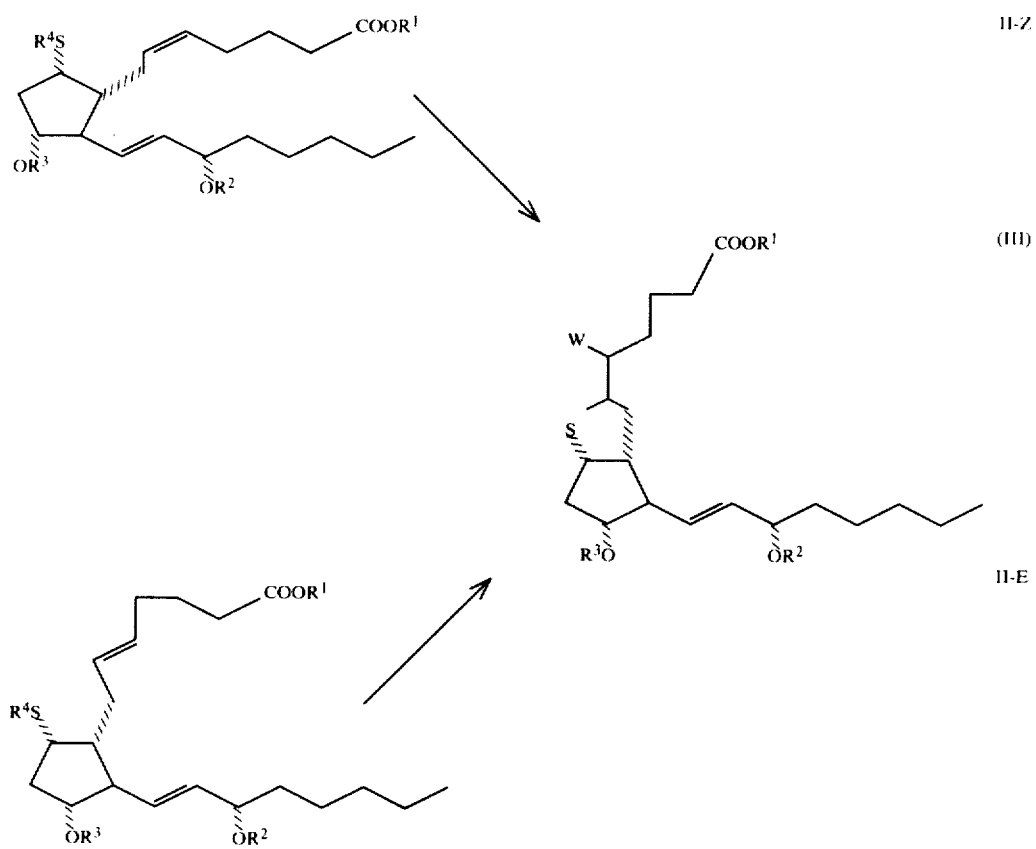

wherein $R^1$, $R^2$, $R^3$ and $R^4$ represent appropriate protecting groups for carboxy, hydroxy and thiol functionalities and W represents hydrogen, halide or a phenyl selenenyl group. The choice of protecting groups depends on the particulars of the reaction conditions and starting materials as will be described hereinafter. $R^1$ can be any carboxy protecting functionality, such as alkyl, with chain length $C_1$–$C_{10}$, preferably $C_1$–$C_4$, most preferably methyl or ethyl. $R^2$ and $R^3$ are hydrogen or base- or acid-sensitive hydroxy protective functionalities such as acetyl, propionyl, butyryl, substituted acyl such as trifluoroacetyl, trichloroacetyl, trialkyl silyl, such as trimethylsilyl, dimethyl tert-butylsilyl, triethylsilyl and tert-butyldiethylsilyl; or ether, such as tetrahydropyranyl. Preferably $R^2$ and $R^3$ are acetyl, tert-butyldimethylsilyl, tetrahydropyranyl or hydrogen depending on the reaction conditions; most preferably, $R^2$ and $R^3$ are acetyl or tert-butyldimethylsilyl. $R^4$ is hydrogen or an acid- or base-sensitive thiol protecting functionality, such as acetyl, propionyl, trifluoroacetyl and benzoyl. Preferably $R^4$ is hydrogen or acetyl, most preferably $R^4$ is acetyl.

When the cyclization is carried out in the presence of acids, the useful acids are dilute inorganic acids such as dilute hydrochloric, nitric, sulfuric and perchloric or organic acids such as acetic, propionic, p-toluenesulfonic, trifluoroacetic and trichloroacetic; preferably, organic acids are used, most preferably acetic acid. When the cyclization is carried out in the presence of halogens, chlorine, bromine or iodine can be used, most preferably iodine. In this case it is preferred to carry out the reaction in the presence of a base. When the cyclization is carried out with phenylselenyl halides, the useful reagents are phenylselenenylbromide, chloride, or fluoride, preferably bromide or chloride, most preferably chloride. Other selenenyl halides can be used, such as methylselenenyl halides, propylselenenyl halides, methylphenylselenenyl halides and halophenylselenenyl halides. The reaction may be carried out in the absence of oxygen, in which instance, the reaction mixture is degassed by standard degassing techniques and run under vacuum or under an inert atmosphere. Gases such as nitrogen or rare gases such as helium and argon can be used to provide an inert atmosphere. The products of the cyclization reaction, cyclic thioethers of formula III, are purified by standard techniques, well-known to those skilled in the art. These techniques include high pressure liquid chromatography, silica gel column chromatography, alumina gel column chromatography, thin layer chromatography and preparative gel chromatography. The solvents useful in this cyclization reaction are water, alcohols, such as methanol, ethanol, propanol and isopropanol; inert organic solvents such as halogenated hydrocarbons, e.g., methylene chloride, chloroform, carbon tetrachloride or dichloroethane; ethers such as diethyl ether, di-isopropyl ether, tetrahydrofuran and mixtures thereof. Preferably the reaction temerature depends on the nature of the starting materials and solvents, but may be as low as −78° C. or as high as 50° C.

The starting materials for the cyclization reaction, I-Z and II-E, can be prepared by the following sequence of reactions from common intermediate IV-Z:

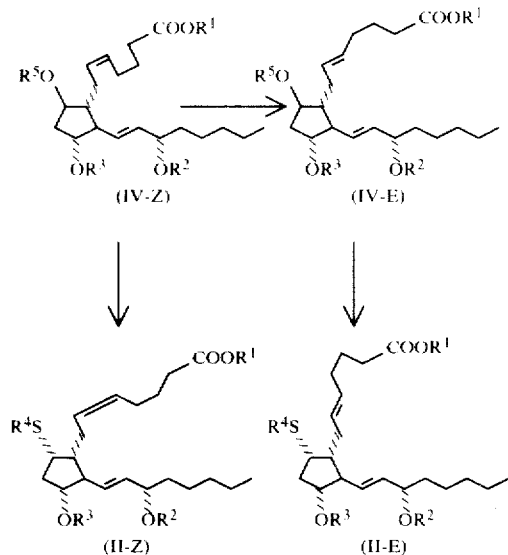

Since the II-Z and II-E derivatives ($R^1$, $R^2$, $R^3$, $R^4$ = appropriate protecting groups, supra) are simple double bond isomers of each other, it is possible to produce either from IV-Z ($R^5$ = appropriate protecting group, infra), which is a 5(Z), 9α-oxy $PGF_{2\alpha}$ ester derivative. The preparation of IV-Z can be made by a variety of reactions, infra. The transformation of IV-Z (cis isomer at C-5) into IV-E (trans isomer at C-5) can be carried out by standard double bond isomerization reactions, well known to those skilled in the art. Such reactions include, for example, photochemical isomerizations.

The photochemical transformation of IV-Z (5-cis isomer) to IV-E (5-transisomer) is carried out using well known photochemical techniques. The protecting groups for the starting material are chosen so as to minimize side reactions and allow easy recovery of final products. $R^5$ is preferably a group that will render the resulting 9β-oxy derivative reactive towards nucleophilic substitution reactions by sulfur nucleophiles; in other words, the resulting $R^5O$-group should be a good leaving group, preferably better in leaving ability than the $R^2O$- and $R^3O$-groups. Examples of functions that can be used for $R^5$ include, but are not limited by, organic sulfonyl derivatives, organic phosphoryl derivatives, and organic phosphonyl derivatives. Preferred $R^5$ groups are organic sulfonyl derivatives, most preferred is p-toluenesulfonyl or methane sulfonyl

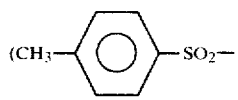

or $CH_3-SO_2-$). The appropriately protected starting 5(Z), 9α-oxy $PGF_{2\alpha}$ alkyl ester derivative (IV-Z) can be easily prepared from the deprotected precursors by well known reactions. In order to impart selectivity in the introduction of the $R^2$, $R^3$ and $R^5$ groups, these groups are introduced at different times during the formation of the intermediate IV-Z. The sequence and order to introduction of the protecting groups will be discussed infra, when describing the synthesis of IV-Z itself. The photochemical isomerization of IV-Z into IV-E is carried out in inert organic or inorganic solvents such as water, alcohols such as methanol or ethanol, hydrocarbons such as benzene or toluene, or polar aprotic solvents such as DME, DMF, DMSO, acetonitrile. Preferred solvents are benzene or toluene, most preferred is benzene. The reaction can be carried out in the presence of a free radical initiator such as diphenyldisulfide or dibenzoylperoxide. The most preferred initiator is diphenyldisulfide. The reaction is carried out in the absence of oxygen, under vacuum or in the presence of an inert gas such as nitrogen, or rare gases. Most preferred is to carry out the reaction in a degassed solution. The temperature of the reaction can be in the range of from −50° C. to +30° C., preferred range is 0° to 25° C., most preferred temperature is 20° C. The ratio of starting material IV-Z to free radical initiator is from 1:0.1–1, preferred 1:0.1–0.6, most preferred is 1:0.5. The length of the reaction is in the range 1–15 hours, preferably 2 to 6 hours, most preferably 4 hours. Irradiation is done with standard commercial photochemical equipment, at wavelengths in the ultraviolet range. After the reaction has proceeded for the chosen length of time, there is obtained an equilibrium mixture of 5(E), 9β-oxy and 5(Z), 9β-oxy $PGF_{2\alpha}$ alkyl ester derivatives (IV-E and IV-Z), with the 5(E) isomers usually predominating.

The separation of the 5(E) and 5(Z) isomers, carried out in order to obtain pure IV-E and to recover starting IV-Z for recycling purposes can be done by standard purification techniques. The most preferred technique is a silver nitrate-impregnated silica gel column. The yield of 5(E) isomer IV-E is 60–90%, usually about 80% and the purity is satisfactory.

It will be obvious to anyone skilled in the art that the photochemical isomerization of the C-5 double bond can be carried out at the level of isomer II-Z. The reaction is not dependent on the exact configuration around asymmetric centers at C-9, C-11 and C-15 and can be carried out on any configuration of said asymmetric center or combinations thereof.

For other, similar photochemical isomerizations in the prostaglandin field see, for example, Corey, et al (Tetr. Letters, 3529 (1977), and Schneider et al (J. Amer. Chem. Soc., 99, 1222 (1977)).

The transformation of isomers IV into isomers II involves a nucleophilic displacement reaction with inversion at carbon C-9 of IV, to change its configuration from 9β to 9α. This nucleophilic displacement reaction is independent of the configuration of the double bond at C-5 so that the reaction can be described once for both IV-Z and IV-E isomers. The sulfur nucleophile used in the reaction includes thioacyl derivatives of the formula

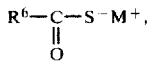

where $R^6$ is alkyl such as methyl, ethyl or propyl, aryl such as phenyl, tolyl and $M^+$ is an alkali metal cation such as $Na^+$, $K^+$, $Li^+$. Preferred nucleophilic reagents are potassium salts, most preferred reagent is potassium thioacetate ($CH_3COSK$). The ratio of starting material IV to thioacylate nucleophile is 1:20, preferably 1:10, most preferably 1:5. The transformation IV→II is carried out in polar solvents which are conducive to SN$_2$ reactions; preferred solvents are polar aprotic solvents such as DMSO, DMF, HMPA, acetonitrile, most preferred solvent is DMSO. The temperature of the reaction is in the range 25°-80° C., preferred range is 30°-50° C., most preferred temperature is 45° C. The length of the reaction time is in the range of 12 hours to 2 days, preferably 24 hours. The yield is excellent in most cases, 85% or better.

Intermediate IV-Z which is an appropriately substituted 5(Z), 9α-oxy PGF$_{2α}$ alkyl ester derivative can be readily obtained from an appropriately protected PGE$_2$ alkyl ester such as V-Z or an appropriately protected PGF$_{2α}$ alkyl ester.

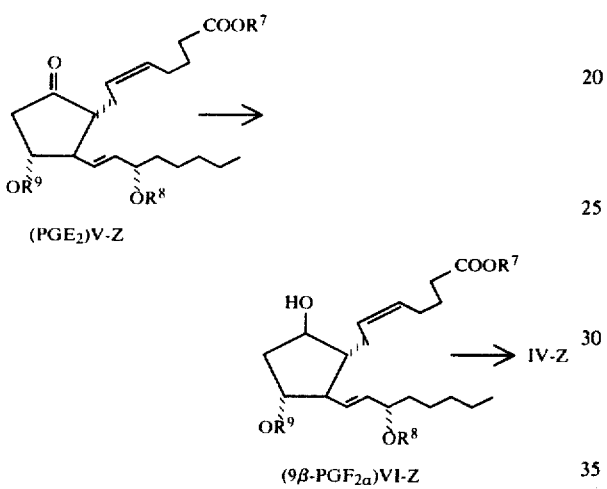

Precursor V-Z (R$^7$=—CH$_3$, R$^8$=—COCH$_3$, R$^9$=H) can be prepared by a known literature method (Corey et al, Proc. Nat. Acad. Sci., 72, 3355 (1975); Bundy et al, J. Amer. Chem. Soc., 94, 2123 (1972)). The groups R$^7$, R$^8$ and R$^9$ however, need not be limited to those described in the aforementioned references, but may be any of those described supra for the intermediate IV-Z. It is useful to protect the C-11 hydroxy position with an acetyl or tetrahydropyranyl (THP) group, preferably tetrahydropyranyl. The reduction of the appropriately protected PGE$_2$ derivative V-Z to the PGF$_{2α}$ derivative VI-Z is carried out using standard reduction reagents and techniques. Reducing agents such as NaBH$_4$ or Zn(BH$_4$)$_2$ can be used, preferably Zn(BH$_4$)$_2$. The solvent, reaction temperatures, reaction times, and reactant ratios are well described in the organic literature and will not be further discussed. The product of the reduction is VI-Z; it is obtained as a mixture of 2 diastereomers α and β with opposite configurations at C-9. The ratio of 9α (undesired isomer) to 9β (desired isomer) is about 1:1 and the total yield is usually better than 95%. The 9α and 9β isomers can be separated by chromatographic techniques such as those described supra for the separation of IV-Z from IV-E. Finally, the partially protected PGF$_{2α}$ derivative VI-Z is transformed to the fully protected derivative IV-Z by reaction with an organic sulfonyl halide such as mesylchloride or tosylchloride. The reaction of hydroxy derivatives with acyl halides is well known in the art and will not be described further. (R. Morrison and R. Boyd, Organic Chemistry, 2nd Ed., p. 527). Another method of preparing the required precursor IV-Z is to use well known PGF$_{2α}$ alkyl ester derivatives such as 11,15-bis(THP) ether PGF$_{2α}$ methyl ester as starting materials, (Corey et al, J. Amer. Chem. Soc., 92, 397 (1970)). The transformation of this material to the desired PGF$_{2α}$ derivative VI-Z is by epimerization at carbon C-9 from the α to the β configuration. As described supra, the protecting groups R$^1$, R$^2$ and R$^3$ need not be limited to those described in the Corey et al reference, but may be chosen from a larger number.

The epimerization of the C-9 carbon from 9α to 9β configuration is carried out by first transforming the 9 hydroxy group of 11,15-bis(THP)-PGF$_{2α}$ methyl ester to a good leaving group, preferably a mesylate, using the acyl chloride method under standard esterification conditions supra. The C-9α-center is then transformed to the C-9β-hydroxy derivative VI-Z using the known technique of displacement with potassium superoxide (Corey et al, Chem. Comm., 658 (1975)). The VI-Z derivative is then transformed by acylation with mesyl or tosyl chloride to the IV-Z derivative: a bis-11,15(THP) ether, 9β-mesylate PGF$_{2α}$ methyl ester.

If it were necessary to change the protecting groups on intermediate IV-Z before continuing to IV-E by photochemical isomerization on to II-Z by thioacetate replacement, the deprotection/reprotection intermediate steps can be carried out easily by following standard practice in the field of organic chemistry.

The reactions used to transform III to the final thia-prostacyclin products are dependent on the nature of the group W and the protecting groups R$^1$, R$^2$ and R$^3$. These reactions will be different for different starting materials.

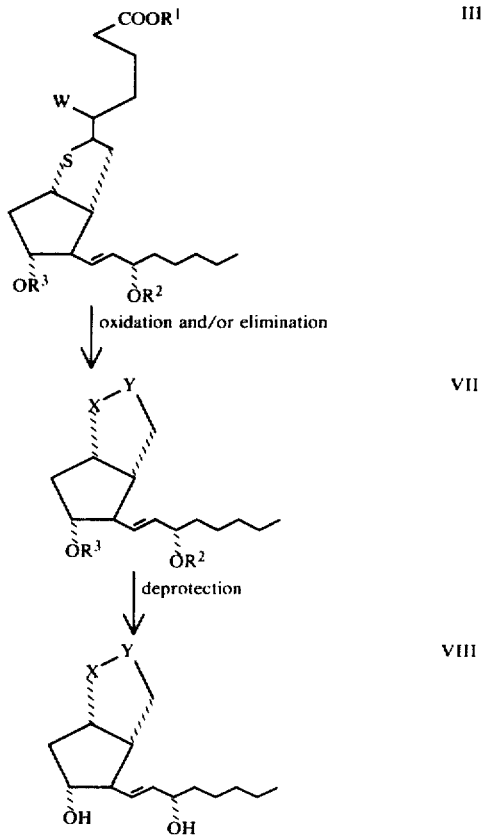

The nature of the group W has been defined supra as being hydrogen, phenylselenenyl ($C_6H_5$-Se-) or halide (e.g., I-). X is =S, =SO or >$SO_2$; Y is (E)-and(Z)->C=CH—$CH_2CH_2CH_2COOR^1$, (E)->CH—CH=CH—$CH_2CH_2COOR^1$ or >CH—$CH_2CH_2CH_2CH_2COOR^1$; and $R^1$, $R^2$, $R^3$ are defined supra. When W is hydrogen, the compound III itself is simply deprotected in dilute acid or base to yield one of the products of the present invention, VII (X=>S, Y=->CH—$CH_2CH_2CH_2CH_2COOR^1$). When W=hydrogen, compound III can be mildly oxidized to yield the 6,9α-sulfoxa-5,6-dihydroprostacyclin derivative VII (X=>SO) or it can be strongly oxidized to yield the 6,9α-sulfo-5,6-dihydroprostacyclin derivative VII (X=>$SO_2$). The mild oxidation treatment is carried out with close to stoichiometric amounts of an oxidizing agent such as m-chloroperbenzoic acid, trifluoromethylperacetic acid or $H_2O_2$. It is preferred to use m-chloroperbenzoic acid or $H_2O_2$, most preferred is m-chloroperbenzoic acid. It is critical that the molar ratio of oxidizing agent to derivative III not exceed 1.2:1, preferably 1.1:1 since increasing amounts of higher oxidation products are otherwise obtained. The temperature of the reaction depends on the oxidizing agent and can be from −80° to +25° C. The preferred temperature range for m-chloroperbenzoic acid is −90° to −50° C., most preferred −78° C. The useful solvents are chlorinated hydrocarbons such as chloroform, carbon tetrachloride, methylene chloride, preferred are chloroform or methylene chloride, most preferred is methylene chloride. The strong oxidation treatment is carried out with an excess of one oxidizing agent or mixtures of oxidizing agents, wherein the molar ratio of compound III to oxidizing agent is 1:5–50, preferably 1:10–20, most preferably 1:10. The reaction is carried out in the presence of diphenyldiselenide ($\phi SeSe\phi$) presumably to aid in the oxidation, by the formation in situ, of

$C_6H_5SeOOH$.

Solvents, temperatures and reaction times can be easily adjusted according to the needs of the reaction. After deprotection of the corresponding intermediates (VII), the products of the present invention are obtained, VIII (X=>SO, Y=>CHCH$_2$CH$_2$CH$_2$CH$_2$COOR (by mild treatment); X=>$SO_2$, Y=>CHCH$_2$CH$_2$CH$_2$CH$_2$COOR (by strong treatment)). It should be noted that when X=>SO, there are obtained 2 diastereoisomers which can be separated to yield 2 distinct products.

When W=halide in intermediates III, the resulting compounds are treated with a base to eliminate hydrogen halide and yield intermediates VII (X=>S, Y=>C=CH—$CH_2CH_2CH_2COOR^1$). Any organic solvent-soluble base is useful in this dehydrohalogenation. Preferred is DBU, sodium ethoxide or sodium methoxide; most preferred is DBU. After deprotecting the 11 and 15 hydroxy positions if necessary, the product VIII of the present invention is obtained (X=>S, Y=>C=CH—$CH_2CH_2CH_2COOR$). It should be noted that in the dehydrohalogenation, 2 possible geometric double bond isomers can be obtained, $C_5$-cis- and $C_5$-trans, depending on the geometrical configuration of the starting $PGF_{2\alpha}$ compounds II.

When W=$C_6H_5$-Se- in intermediate III, treatment with close to stoichiometric amounts of an oxidizing agent such as m-chloroperbenzoic acid (MCPBA) at low temperatures yields intermediate VII, which after deprotection in acid or base, if necessary, yields the 6,9-sulfoxa prostacyclin VIII (X=>SO, Y=>C=CH—$CH_2CH_2CH_2COOR$). Treatment of intermediate III (W=$C_6H_5$—Se—) with 3.3 equiv. of MCPBA at −78°→25° C. followed by appropriate deprotection, if necessary, yields 6,9-sulfo-prostacyclin product VIII (X=>$SO_2$, Y=>C=CH—$CH_2CH_2CH_2COOR$). Treatment of intermediate III (W=$C_6H_5$—Se—) with an excess of an oxidizing agent such as $H_2O_2$, at close to room temperature, followed by appropriate deprotection, if necessary, yields 6,9-sulfo-4(E) isoprostacyclin compound VIII (X=>$SO_2$, Y=>CH—CH=CH—$CH_2CH_2COOR$). It is presumed that the m-chloroperbenzoic acid treatment at low temperatures achieves the observed selectivity for the production of the conjugated sulfoxides and conjugated sulfones by causing oxidation of the sulfur first, followed by selenium oxidation. This selectivity is lost when using $H_2O_2$ due to the rather indiscriminate order in which sulfur and selenium are oxidized; thus, in the $H_2O_2$ method at room temperatures the 4(E)-6,9-sulfo isoprostacyclin is obtained along with the 6,9-sulfoprostacyclin.

Preparation of the 6,9α-thiaprostacyclin VIII (X=>S, Y=>C=CH—$CH_2CH_2CH_2COOR$) can also be carried out by reducing the the corresponding 6,9-sulfoxide VIII (X=>SO) with a reducing agent such as $(CH_3)_3SiI$ in $CCl_4$ in the presence of a base such as pyridine.

It should be noted that when the sulfoxide products VIII (X=>SO) are prepared, 2-distinct diastereoisomers are obtained due to the rigid configuration of the sulfoxide center. These isomers can be separated and purified by standard analytical methods. In addition, upon preparation of the 6,9-sulfoxa- or 6,9-sulfo-analogs containing a double bond at position C-5 (X=>SO or >$SO_2$; Y=>C=CH—$CH_2CH_2CH_2COOR$), the double bond can exist in the cis- or trans-configurations. It is observed that when the phenyl selenenyl halide method of synthesis of the products, proceeds via acyclic intermediates IV-Z, the 5(E) configuration in the final prostacyclin products is obtained. Alternatively, when the selenenyl method of synthesis of the products proceeds via acyclic intermediates IV-E, the 5(Z) configuration in the final prostacyclin products is obtained. The exact opposite results are obtained when using the halogen cyclization method. This stereospecificity obviates separation and purification of final products. Since the natural prostacyclin I has the 5(Z) configuration, the present synthetic methodologies open the path to the preparation of sulfur analogs with the natural or with the opposite configurations at C-5. The prostacyclin sulfur analogs of the present invention are more stable in solution than the natural prostacyclin I. (Table I).

Pharmacological testing of the thiaprostacyclin derivatives of the present invention has shown that they are useful as inhibitors of blood platelet aggregation, as antagonists for natural prostacyclin and have biological effects on cat coronary artery.

Effects of prostacyclin analogs on platelet aggregation was evaluated using human and rabbit citrated platelet-rich plasma in a chronolog aggregometer at 37°. Each of the analogs was treated at two concentrations (20 mM and 2 μM) for agonistic activity (inhibition of aggregation induced by 2 μM ADP) and antagonistic activity (prevention of the inhibition of ADP-induced aggregation by 5 mM prostacyclin).

Effects of prostacyclin analogs on isolated perfused cat coronary arteries were measured as follows.

Cats of either sex (2.5–3.5 kg) were anesthetized with sodium pentobarbital (30 mg/kg) given intravenously. Hearts were rapidly excised and placed in oxygenated (95% $O_2$+5% $CO_2$) ice-cold Krebs-Henseleit (K-H) solution of the following millimolar composition: NaCl, 118; KCl, 4.75; $CaCl_2.H_2O$, 2.54; $KH_2PO_4$, 1.19; $MgSO_4.7H_2O$, 1.19; $NaHCO_3$, 12.5; glucose, 10.00. A 20-gauge stainless steel cannula was inserted into the right coronary artery via the coronary ostium. Distal to the cannula, approximately 1 cm of coronary artery was dissected free of surrounding tissue. The section of right coronary artery with the cannula in place was excised from the heart and immediately transferred to a constant flow perfusion apparatus.

The perfusion apparatus consists of a reservoir containing 20 ml of warm (37° C.) oxygenated (95% $O_2$+5% $CO_2$) K-H solution which bathes the coronary artery and serves as recirculating perfusate. An increase in perfusion pressure indicates vasoconstriction, whereas a decrease in perfusion pressure signifies vasodilation. Following an initial 1 hr. equilibrium period, vascular responsiveness was established by adding 25 mM KCl. After washing with fresh K-H solution for 20–30 mins., the preparation achieved a relatively constant low basal tone. Basal perfusion pressure averaged 50±2.5 mm Hg. Fresh K-H dilutions of stock prostacyclin analog concentrations were added to the perfusate reservoir in 0.1–0.2 ml volumes. Changes in perfusion pressure in response to prostacyclin analog addition generally plateaus within 5 min. of administration. Results are summarized in Table I.

The analogs of the 5(Z) configuration generally show bioactivity in vitro while the analogs of the 5(E) configuration do not. The biological activity itself is an unexpected combination of effects. While the active analogs show inhibition of blood platelet aggregation or antagonistic activity towards natural prostacyclins, they also show vasoconstrictor activities, as seen with natural thromboxane or endoperoxide. The combination of these biological effects render the sulfur analogs of prostacyclins as useful in the treatment of platelet clump dissolution, treatment of thrombosis, treatment of artherosclerosis, treatment of vascular complications in diabetes, hypertension, hypotension, and other related diseases.

The compounds of this invention can be administered by any means that effects palliating conditions of cardiovascular complications in warm-blooded animals. For example, administration can be parenterally, subcutaneously, intravenously, intramuscularly or intraperitoneally. Alternatively or concurrently, administration can be by the oral route. The dosage administered will be dependent upon the age, health and weight of the recipient, kind of concurrent treatment if any, frequency of treatment, and the nature of the effect desired. Generally, daily dosage of active ingredient compounds will be from about 0.5 to 50 mg per kg of body weight. Normally, from 1 to 30 mg per kg per day, in one or more applications per day is effective to obtain the desired result. The compounds can be employed in dosage forms such as tablets, capsules, powder packets, or liquid solutions, suspensions, or elixirs, for oral administration, or sterile liquid formulations such as solutions or suspensions for parenteral use. In such compositions, the active ingredient will ordinarily always be present in an amount of at least 0.5% by weight based on the total weight of the composition and not more than 90% by weight.

TABLE I

| Product | Z ½ Saline 250° C. | Biological Activity | |
|---|---|---|---|
| | | Platelet Aggregation | Cat Coronary Artery |
| Natural Prostacyclin | 2 minutes | (1) Inhibitor (P) | Dilator (P) |
| 6,9-α Thia-5(Z)prostacyclin | >3 hours | (0.2–0.5) Inhibitor (P) | Constrictor (P) |
| 6,9-sulfoxa-5(E)prostacyclin | >24 hours | Very little activity, if any | Very little activity, if any |
| 6,9-sulfoxa-5(Z)prostacyclin | >24 hours | Little activity | Little activity |
| 6,9-sulfo-5(E)prostacyclin | >24 hours | Very little activity, if any | Very little activity, if any |
| 6,9-sulfo-5(Z)prostacyclin | >24 hours | Little activity | Little activity |
| 6,9-thia-5,6 dihydroprostacyclin | >24 hours | Little activity | Constrictor (M) |
| 6,9-sulfoxa-5,6 dihydroprostacyclin | >24 hours | Antagonist of prostacyclin (M) | Constrictor (M) |
| 6,9-sulfo-5,6 dihydroprostacyclin | >24 hours | Antagonist of prostacyclin (M) | Constrictor (M) |
| 6,9-sulfo-4(E)isoprostacyclin, 6α isomer | >24 hours | Antagonest of prostacyclin (M) | Constrictor (M) |
| 6,9-sulfo-4(E)isoprostacyclin, 6β isomer | >24 hours | Inhibitor | Constrictor (M) |

(P) = Potent
(M) = Moderate (n concentrations 10⁻⁶ molar)
Very little activity means at concentrations < 10⁻⁶M; compounds may show more activity at concentrations > 10⁻⁶M.

Having generally described the invention, a more complete understanding can be obtained by reference to certain examples, which are included for purposes of illustration only and are not intended to be limiting unless otherwise specified.

EXAMPLE I

Preparation of 6,9α-thia-5(Z) prostacyclin, sodium salt 425 mg of the methyl ester of 15-acetoxy $PGE_2$(V-Z, $R^1$=—$CH_3$, $R^2$=

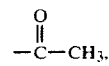

$R^3$=H; Corey et al, P.N.A.S., USA, 72, 3355 (1975)) was dissolved in 12 ml of methylene chloride and to the solution was added 218 mg (1.5 equiv.) of dihydropyran and 0.46 mg (0.2 mole %) of p-toluenesulfonic acid at 25° C. After stirring for 0.5 hours, the reaction was stopped and 100% yield of the 11-THP, 15-acetoxy $PGE_2$methyl ester was obtained (V-Z, $R^7$=—$CH_3$, $R^8$=

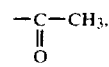

$R^9$=THP). 0.535 gm of the 11-THP, 15-acetoxy $PGE_2$-methyl ester thus obtained was dissolved in 12 ml of DME at 25° C. and treated with an excess (1.5 equivalents) of zinc borohydride for 15 hours. After isolation and purification, a 95% yield of a mixture of 9α and 9β-PGF$_{2\alpha}$ was obtained (9β:9α ratio ~55:45). The desired 9β-PGF$_{2\alpha}$ isomer (VI-Z, R$^7$=—CH$_3$, R$^8$=—COCH$_3$, R$^9$=THP) was obtained by chromatographic separation from the 9α isomer on silica gel with ether as solvent. The 9β-PGF$_{2\alpha}$ isomer thus obtained was then transformed into the 9β mesylate-PGF$_{2\alpha}$ methyl ester (IV-Z, R$^1$=—CH$_3$, R$^2$=

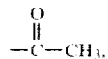

R$^3$=—THP, R$^5$=—SO$_2$CH$_3$). This reaction was carried out by dissolving 0.190 gm of the 9β-PGF$_{2\alpha}$ methyl ester VI-Z in 4 ml of methylene chloride at −20° C., adding methanesulfonyl chloride (53 mg., 1.2 equiv.) in the presence of triethylamine (1.2 equiv.). After stirring for 30 minutes, the product 9β-mesylate was extracted and purified. When the 9β-mesylate PGF$_{2\alpha}$ methyl ester (0.19 gm) thus obtained was treated with potassium thioacetate (0.38 gm, 10 equivs) in 2 ml of DMSO, at 45° C., for 24 hours, the thioacetate II-Z (R$^1$=—CH$_3$, R$^2$=R$^4$=

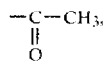

R$^3$=—THP) was obtained in 90% yield. Removal of the tetrahydropyranyl group R$^3$ was carried out in acetic acid-THF-water (3:2:2) at 45° for 20 hours and resulted in the formation of the diacetate II-Z (R$^1$=—CH$_3$, R$^2$=R$^4$=

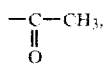

R$^3$=H) in 98% yield. Treatment of this diacetate with anhydrous potassium carbonate (4 equivalents) in absolute methanol at 25° C. for 2 hours, gave an 83% yield of 9α-thio-PGF$_{2\alpha}$ methyl ester (II-Z, R$^1$=—CH$_3$, R$^2$=R$^3$=R$^4$=H).

The cyclization of 9α-thio-PGF$_{2\alpha}$ methyl ester is carried out smoothly by addition of iodine (1.1 equivalents) to a methylene chloride solution containing the thio starting material, in the presence of potassium carbonate (2 equiv.) at −40°. This reaction led to the 5-iodo, 6,9α thio-5,6-dihydroprostacyclin methyl ester III (R$^1$=—CH$_3$, R$^2$=R$^3$=H, W=—I) as the major product in 55% yield. The iodothioether III was then exposed to excess 1,5-diazabicyclo[5.4.0]undec-5-ene (DBU) in benzene at 25° for 1 hour and transformed cleanly and in essentially quantitative yield to 5(Z)-6,9-thioprostacyclin methyl ester VII (X=>S; Y=(Z)->C=CH—CH$_2$CH$_2$CH$_2$CO$_2$CH$_3$). Hydrolysis of this methyl ester in 90% ethanol containing sodium ethoxide (5 equiv.) afforded, quantitatively, stable solutions of the final product 5(Z)-6,9α-thioprostacyclin as its sodium salt, ready for bioassays (VIII, X=>S; Y=(Z)->C=CH—CH$_2$CH$_2$CH$_2$CO$_2$Na). Both the acid VIII and the methyl ester VII could be isolated from pH 4 buffers by extraction with ether. They could be easily chromatographed on silica gel without appreciable decomposition.

The methyl ester VII showed the following characteristics. m.p. oil; $^1$H nmr data: 220 MHz, CDCl$_3$;τ4.50 (m, 2H, olefin) τ4.72 (m, 1H, thioenol ether); i.r. data: CCl$_4$, ν max (1730 cm$^{-1}$, ester); solubility data: organic solvents.

EXAMPLE 2

Preparation of 5(Z)-6,9α-sulfoxaprostacyclin sodium salt

The starting material for this synthesis is 11,15-bis(tetrahydropyranyl)ether PGF$_{2\alpha}$ methyl ester (Corey, et al, J. Amer. Chem. Soc., 92, 397 (1970)). This compound was transformed to the 9α mesylate 11,15 bis (THP) ether PGF$_{2\alpha}$ methyl ester via reaction with methanesulfonyl chloride (3 eqs.) in methylene chloride at −20° C. for 0.5 hours. The so obtained mesylate was transformed to the 9β-hydroxy epimer PGF$_{2\alpha}$ methyl ester VI-Z (R$^7$=—CH$_3$, R$^8$=R$^9$=THP) with potassium superoxide (16 equivs.) in DMSO in the presence of 18-Crown-6 at 20° C. for 12 hours. The 9β-hydroxy PGF$_{2\alpha}$ isomer was then reacted with methanesulfonyl chloride (as in example 1), to yield the 9β-mesylate IV-Z (R$^1$=—CH$_3$, R$^2$=R$^3$=THP, R$^5$=—SO$_2$CH$_3$) in 100% yield. This compound was then deprotected in acetic acid-THF-water (3:2:2) at 45° C. to give the diol IV-Z (R$^1$=—CH$_3$, R$^2$=R$^3$=H, R$^5$=—SO$_2$CH$_3$) and reprotected with tert-butyldimethyl silylchloride (4 eqs.)-imidazole-DMF at 25° C. to afford the 9β-mesylate bis(silyl)PGF$_{2\alpha}$ methyl ester IV-Z (R$^1$=—CH$_3$, R$^2$=R$^3$=

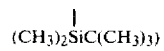

in 90% yield. Irradiation of this bis(silyl)ether with UV light (255 nm) in the presence of diphenyldisulfide (0.5 equivs.) in degassed benzene solution at 20° C. for 4 hours, gave an equilibrium mixture of 5(E)- and 5(Z)-isomers (IV-E and IV-Z; R$^1$, R$^2$ and R$^3$ as above). The 5(E) isomer predominated (ca 85:15). Column chromatography on silver nitrate-impregnated silica gel led to isolation of pure 5(E)mesylate IV-E (R$^1$, R$^2$, R$^3$ as above), (80%). Exposure of the thus obtained intermediate IV-E to excess KSCOCH$_3$ in DMSO at 45° C. for 24 hours, furnished the 9α-thioacetate II-E (R$^1$, R$^2$, R$^3$ as above, R$^4$=

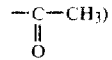

in 86% yield. On treatment with phenylselenenyl chloride (1.2 eqs.) in dry methanol at −78° C. for 1 hour, the thioacetate cyclized smoothly to the phenylselenothioether III in 68% yield (R$^1$, R$^2$ and R$^3$ as above, W=C$_6$H$_5$—Se—). This chromatographically and spectroscopically homogeneous material is assumed to be a single diastereoisomer and is different from the one obtained in a similar manner from the corresponding 5(Z)-thioacetate PGF$_{2\alpha}$ methyl ester IV-Z (R$^1$, R$^2$, R$^3$ as above, R$^4$=—COCH$_3$). When the selenothioether III (R$^1$, R$^2$, R$^3$ as above, W=C$_6$H$_5$Se—) was heated in acetic acid-THF-H$_2$O (3:2:2) at 45° C. for 15 hours, disilylation occurred and the diol thioether III (R$^1$=—CH$_3$, R$^2$=R$^3$=H, W=C$_6$H$_5$Se—) was formed quantitatively.

The selenothioether thus obtained gave, on treatment with 2.2 equivalents of m-chloroperbenzoic acid in methylene chloride at $-78° \rightarrow 0°$ C. the 6,9α-sulfoxaprostacyclin methyl ester VII (X=>SO, Y=>C=CH—CH$_2$CH$_2$CH$_2$CO$_2$CH$_3$) (78% yield) and as a mixture of 2 isomers. These isomers can be easily separated by preparative layer chromatography on silica gel (5% methanol in CH$_2$Cl$_2$) to give pure sulfoxides.

The same sulfoxides can be obtained by treating the 6,9α-thioprostacyclin methyl ester obtained from Example 1, with excess H$_2$O$_2$. The sulfoxide methyl esters were then hydrolyzed in 90% ethanol with sodium hydroxide at 25° C. to afford the stable solutions of the sodium salts VIII (X=>S—O; Y=>C=CH—CH$_2$CH$_2$CH$_2$CO$_2$Na). Acidification of these compounds in aqueous solutions leads to the corresponding acids which can be extracted with ether and purified chromatographically.

EXAMPLE 3

Preparation of 5(Z)-6,9α-sulfoprostacyclin sodium salt

The critical intermediate for this synthesis is 11,15-diol, 5-phenylseleno, 6,9α-thiaprostacyclin methyl ester III (R$^1$=—CH$_3$, R$^2$=R$^3$=H, W=C$_6$H$_5$—Se—). The preparation of this intermediate is described in Example 2. When this intermediate was oxidized with 3.3 equivalents of m-chloroperbenzoic acid in methylene chloride at $-78°$ C. to 25° C. for 12 hours, the 6,9α-sulfoprostacyclin methyl ester VII was produced in 81% yield (VII, X=>SO$_2$; Y=>C=CH—CH$_2$CH$_2$CH$_2$CO$_2$CH$_3$). It was isolated by prep layer chromatography and hydrolyzed with NaOEt in 90% ethanol at 25° C. to afford the corresponding sodium salt VIII (X=>SO$_2$, Y=>C=CH—CH$_2$CH$_2$CH$_2$CO$_2$Na). The salt was quantitatively stable in aqueous solution and gave, by acidification, the corresponding acid which could be extracted with ether and purified chromatographically.

Analytical data for methyl ester: $^1$H nmr, 220 MHz, CDCl$_3$:τ4.04 (t, J=8 Hz, 1H, sulfoenol ether); τ4.43 (dd, J=15.5 Hz, 7 Hz, 1H, olefin); τ4.60 (dd, J=15.5 Hz, 8 Hz, 1H, olefin) i.r. spectra: CHCl$_3$, ν max (1120, 1300 cm$^{-1}$, sulfone) (1725 cm$^{-1}$, ester) solubility: CH$_2$Cl$_2$.

EXAMPLE 4

Preparation of 4(E)-6,9α-sulfoisoprostacyclin

The critical intermediate for this synthesis is the 11,15 diol, 5-phenylseleno, 5,6-dihydro 6,9α-thiaprostacyclin methyl ester III (R$^1$=—CH$_3$, R$^2$=R$^3$=H, W=C$_6$H$_5$Se—). The preparation of this intermediate is described in Example 2. When this intermediate was treated by 10 equivalents to H$_2$O$_2$ at 25° C. for 24 hours in THF, 29% yield of the unconjugated 6,9-sulfo-4(E) isoprostacyclin methyl ester was produced (VII, X=>SO$_2$; Y=(E)>CH—CH=CH—CH$_2$CH$_2$CO$_2$CH$_3$). The material could be separated and purified by prep layer chromatography on silica gel, (2.5% methanol in ether, R$_f$=0.06). Base hydrolysis of the methyl ester VII as described for Examples 2 and 3 supra, afforded the corresponding sodium salt.

Analytical data for methyl ester: m.p.: Solid; $^1$H nmr; 220 MHz, CDCl$_3$: τ4.15 (ill defined d, J=15.5 Hz, 1H, olefin); τ4.52 (m, 3H, olefinic); i.r.: CHCl$_3$, ν max (1125, 1310 cm$^{-1}$, sulfone); (1735 cm$^{-1}$, ester); solubility: CH$_2$Cl$_2$

EXAMPLE 5

Preparation of 5,6-dihydro-6,9α-thiaprostacyclin methyl ester

The starting material for this synthesis is 11,15 bis(silyl), 9-thio PGF$_{2α}$ methyl ester derivative II-E (R$^1$=—CH$_3$, R$^2$=R$^3$=

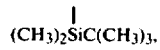

R$^4$=H). This compound can be readily obtained by anaerobic, basic deprotection of the corresponding thioacetate II-E (R$^1$=—CH$_3$, R$^2$=R$^3$=

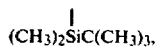

R$^4$=—COCH$_3$) prepared as in Example 2. A degassed solution of the starting material in acetic acid:THF:H$_2$O (3:2:2) was heated at 45° C. for 20 hours to produce directly 6,9-thio-5,6-dihydro-prostacyclin methyl ester (66%) by removal of the silyl ethers and concurrent acid catalyzed cyclization. The product is compound VIII (X=>S; Y=>CH CH$_2$CH$_2$CH$_2$CH$_2$CO$_2$CH$_3$). m.p.: oil; $^1$H n.m.r.; 220 MHz, CDCl$_3$, τ4.50 (m, 2H, olefin); i.r.: neat, ν max 1720 cm$^{-1}$ (ester).

EXAMPLE 6

Preparation of 5,6-dihydro-6,9-sulfo-prostacyclin sodium salt

When the 5,6-dihydro-thioprostacyclin methyl ester (VIII; X=>S, Y=>CH—CH$_2$CH$_2$CH$_2$CH$_2$CO$_2$CH$_3$) prepared in Example 5, was exposed to 0.5 equivalents of diphenyldiselenide and 10 equivalents of hydrogen peroxide in THF at 25° C. for 4 hours, a 93% yield of 6,9-sulfo-5,6-dihydroprostacyclin methyl ester was obtained. After base hydrolysis in 90% EtOH containing sodium ethoxide, the corresponding sodium salt was obtained quantitatively VIII (X=>SO$_2$, Y=>CHCH$_2$CH$_2$CH$_2$CH$_2$CO$_2$Na). The salt is stable and can be used for bioassays. Data on methyl ester: m.p.: solid; $^1$H n.m.r.: 220 MHz, CDCl$_3$, τ(4.70, dd, 1H, olefinic); (4.48, dd, 1H, olefin); i.r.: neat, ν max (1725 cm$^{-1}$, ester); (1100 cm$^{-1}$, 1300 sulfone).

EXAMPLE 7

Preparation of 5,6-dihydro-6,9α-Sulfoxaprostacyclin sodium salt

When the 5,6-dihydro-thiaprostacyclin methyl ester (VIII; X=>S; Y=>CHCH$_2$CH$_2$CH$_2$CH$_2$CO$_2$CH$_3$) prepared in Example 5 was exposed to 1.1 equivalents of m-chloroperbenzoic acid in methylene chloride at $-78°$ C., a 70% yield of 5,6-dihydro-6,9-sulfoxaprostacyclin was obtained. The product was a mixture of 2 isomers which were separated by preparative layer chromatography on silica using 10% methanol in methylene chloride as solvent. A major isomer (R$_f$=0.26) and a minor isomer (R$_f$=0.33) were obtained in a ratio of 2:1.

Basic hydrolysis of any of these two products in 90% ethanol containing 5 equivalents of sodium ethoxide, smoothly produced the corresponding, stable sodium salts VIII (X=>SO; Y=>CHCH$_2$CH$_2$CH$_2$CH$_2$CO$_2$Na).

Analytical data on methyl ester: m.p.: Solid; $^1$H nmr: 220 MHz, CDCl$_3$ (a) $\tau$ (4.54, broads, 2H, olefin); (b) $\tau$ (4.59, dd, 1H, olefin)(4.43, dd, 1H, olefin); i.r.:neat (a) $\nu$ max (1010 cm$^{-1}$ sulfone, sulfoxide); (1735 cm$^{-1}$, ester); (b) $\nu$ max (1005 cm$^{-1}$, sulfoxide); (1730 cm$^{-1}$, ester).

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. Biologically active 6,9α-thiaprostacyclin derivatives having the formula:

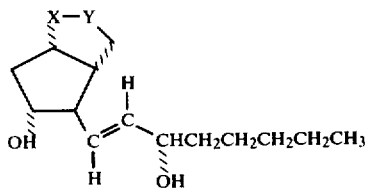

wherein
X represents >S, >SO or >SO$_2$;
Y represents (E) and (Z) >C=CH—CH$_2$CH$_2$CH$_2$COOR; (E)>CH—CH=CH—C$_2$CH$_2$COOR or >CH—CH$_2$CH$_2$CH$_2$CH$_2$COOR; and
R represents a pharmaceutically acceptable cation or a pharmaceutically acceptable lower alkyl group.

2. The prostacyclin derivative of claim 1, wherein X=>S; Y=(Z)->C=CH—CH$_2$CH$_2$CH$_2$CO$_2$R and R=sodium.

3. The prostacyclin derivative of claim 1 wherein X=>S; Y=(Z)->C=CH—CH$_2$CH$_2$CH$_2$CO$_2$R and R=—CH$_3$.

4. The prostacyclin derivative of claim 1, wherein X=>SO; Y=(Z)->C=CH—CH$_2$CH$_2$CH$_2$CO$_2$R and R=Na.

5. The prostacyclin derivative of claim 1, wherein X=>SO; Y=(Z)->C=CH—CH$_2$CH$_2$CH$_2$CO$_2$R and R=—CH$_3$.

6. The prostacyclin derivative of claim 1, wherein X=>SO$_2$; Y=(Z)->C=CH—CH$_2$CH$_2$CH$_2$CO$_2$R and R=Na.

7. The prostacyclin derivative of claim 1, wherein X=>SO$_2$; Y=(Z)->C=CH—CH$_2$CH$_2$CH$_2$CO$_2$R and R=—CH$_3$.

8. The prostacyclin derivative of claim 1, wherein X=>S; Y=>CH—CH$_2$CH$_2$CH$_2$CO$_2$R and R=Na.

9. The prostacyclin derivative of claim 1, wherein X=>S; Y=>CHCH$_2$CH$_2$CH$_2$CH$_2$CO$_2$R and R=—CH$_3$.

10. The prostacyclin derivative of claim 1, wherein X=>SO; Y=>CH—CH$_2$CH$_2$CH$_2$CH$_2$CO$_2$R and R=Na.

11. The prostacyclin derivative of claim 1, wherein X=>SO; Y=>CH—CH$_2$CH$_2$CH$_2$CH$_2$CO$_2$R and R=—CH$_3$.

12. The prostacyclin derivative of claim 1, wherein X=>SO$_2$; Y=>CH—CH$_2$CH$_2$CH$_2$CH$_2$CO$_2$R and R=Na.

13. The prostacyclin derivative of claim 1, wherein X=>SO$_2$; Y=>CH—CH$_2$CH$_2$CH$_2$CH$_2$CO$_2$R and R=—CH$_3$.

14. The prostacyclin derivative of claim 1, wherein X=>SO$_2$; Y=(E)->CH—CH=CH—CH$_2$CH$_2$CO$_2$R and R=Na.

15. The prostacyclin derivative of claim 1, wherein X=>SO$_2$; Y=(E)->CH—CH=CH—CH$_2$CH$_2$CO$_2$R and R=—CH$_3$.

* * * * *